(12) United States Patent
Benshaul

(10) Patent No.: US 11,008,631 B2
(45) Date of Patent: May 18, 2021

(54) KIT AND METHOD FOR COLLECTING BODY FLUID FOR MEDICAL DIAGNOSIS

(71) Applicant: Ilex Medical Ltd., Petach-Tikva (IL)

(72) Inventor: Moshe Benshaul, Tel-Aviv (IL)

(73) Assignee: Ilex Medical Ltd., Petach-Tikva (IL)

( * ) Notice: Subject to any disclaimer, the term of this patent is extended or adjusted under 35 U.S.C. 154(b) by 326 days.

(21) Appl. No.: 15/030,387

(22) PCT Filed: Oct. 22, 2013

(86) PCT No.: PCT/IL2013/050854
§ 371 (c)(1),
(2) Date: Apr. 19, 2016

(87) PCT Pub. No.: WO2015/059686
PCT Pub. Date: Apr. 30, 2015

(65) Prior Publication Data
US 2016/0273059 A1    Sep. 22, 2016

(51) Int. Cl.
*C12Q 1/70*     (2006.01)
*A61B 10/00*   (2006.01)
(Continued)

(52) U.S. Cl.
CPC .......... *C12Q 1/708* (2013.01); *A61B 10/0045* (2013.01); *A61B 10/0096* (2013.01);
(Continued)

(58) Field of Classification Search
CPC . A61B 10/0045; A61B 10/0096; A61B 10/02; A61B 2010/0074;
(Continued)

(56) References Cited

U.S. PATENT DOCUMENTS 1,794,221 A * 2/1931 Washburn ............. A61M 31/00
                                                            15/172
2,847,000 A *  8/1958 Nieburgs ............... A61B 10/02
                                                            600/572
(Continued)

FOREIGN PATENT DOCUMENTS

JP        02100666 A  *  4/1990 ......... A61B 10/0045
WO    WO 2015/059686      4/2015

OTHER PUBLICATIONS

Office Action dated Apr. 30, 2018 From the Intellectual Property, Trademark & Patent Registration Office of Thailand Re. Application No. 1601002200. (2 Pages).

(Continued)

*Primary Examiner* — Sean P Dougherty

(57) ABSTRACT

A kit and method for collecting body fluid for medical diagnosis. In some embodiments, the method includes collecting a sufficient amount of body fluid and cells comprising nucleic acid, and applying a nucleic acid assay to detect pathogenic genomic material such as human papillomavirus mRNA and/or human papillomavirus DNA. In some embodiments, by testing fluid and cells, a sensitivity of the test is improved. In some embodiments, the method includes inserting an absorbing member into a body orifice, such as the vagina, for a time period such as 1-2 hours; retrieving the absorbing member and placing it in a sample container; extracting fluid from the absorbing member using a fluid extraction device, and testing the fluid. In some embodiments, the kit is a home use kit and the sample is self collected by a user.

14 Claims, 11 Drawing Sheets

(51) Int. Cl.
*A61B 10/02* (2006.01)
*B01L 3/00* (2006.01)

(52) U.S. Cl.
CPC ...... *A61B 10/02* (2013.01); *A61B 2010/0074* (2013.01); *A61B 2010/0216* (2013.01); *B01L 3/5023* (2013.01); *B01L 3/5029* (2013.01); *B01L 2300/0832* (2013.01); *B01L 2400/0481* (2013.01); *Y10T 436/25* (2015.01)

(58) Field of Classification Search
CPC . A61B 2010/0216; B01L 3/5029; B01L 3/23; B01L 3/0832; B01L 3/5023
See application file for complete search history.

(56) References Cited

U.S. PATENT DOCUMENTS

| | | | | |
|---|---|---|---|---|
| 3,346,906 | A * | 10/1967 | Harrison | A47L 13/58 15/262 |
| 3,450,129 | A * | 6/1969 | Brewer | A61B 10/02 600/572 |
| 3,712,296 | A * | 1/1973 | Gradone | A61B 10/02 600/572 |
| 3,776,219 | A * | 12/1973 | Brown | A61B 10/0291 600/572 |
| 3,877,464 | A * | 4/1975 | Vermes | A61B 10/0291 600/572 |
| 3,966,558 | A * | 6/1976 | Calva-Pellicer | A61B 10/02 600/572 |
| 4,014,746 | A * | 3/1977 | Greenspan | A61B 10/0096 435/243 |
| 4,232,673 | A * | 11/1980 | Bucalo | A61B 10/0045 600/582 |
| 4,317,454 | A * | 3/1982 | Bucalo | A61B 10/0045 600/572 |
| 4,325,388 | A * | 4/1982 | Bucalo | A61B 10/0045 600/562 |
| 4,409,988 | A * | 10/1983 | Greenspan | A61B 10/0096 435/288.2 |
| 4,596,157 | A * | 6/1986 | Laauwe | G01N 1/12 600/580 |
| 4,789,639 | A * | 12/1988 | Fleming | A61B 10/0096 206/361 |
| 4,813,432 | A * | 3/1989 | Saint-Amand | A61B 10/0096 206/363 |
| 4,877,036 | A * | 10/1989 | Saint-Amand | A61B 10/0096 600/562 |
| 5,129,402 | A * | 7/1992 | Koll | A61B 10/0291 600/572 |
| 5,231,992 | A * | 8/1993 | Leon | A61B 10/0045 128/841 |
| 5,268,148 | A * | 12/1993 | Seymour | A61B 10/0051 422/401 |
| 5,376,337 | A * | 12/1994 | Seymour | A61B 10/0051 422/401 |
| 5,380,492 | A * | 1/1995 | Seymour | A61B 10/0051 422/401 |
| 5,393,496 | A * | 2/1995 | Seymour | A61B 10/0051 422/413 |
| 5,422,273 | A * | 6/1995 | Garrison | A61B 10/0291 422/547 |
| 5,445,164 | A * | 8/1995 | Worthen | A61B 10/0045 600/572 |
| 5,494,646 | A * | 2/1996 | Seymour | A61B 5/411 422/401 |
| 5,528,791 | A * | 6/1996 | Wilson | A47L 13/144 15/119.2 |
| 5,556,376 | A * | 9/1996 | Yoon | A61B 17/00234 604/11 |
| 5,788,097 | A * | 8/1998 | McInnes | A01K 9/005 119/71 |
| 6,013,036 | A * | 1/2000 | Caillouette | A61B 5/00 600/572 |
| 6,150,178 | A * | 11/2000 | Cesarczyk | A61B 10/0045 422/412 |
| 6,174,293 | B1 | 1/2001 | Buck et al. | |
| 6,394,952 | B1 * | 5/2002 | Anderson | G01N 21/474 600/300 |
| 6,475,165 | B1 * | 11/2002 | Fournier | A61B 10/0291 600/562 |
| 6,524,530 | B1 * | 2/2003 | Igarashi | B01L 3/5029 422/411 |
| 6,576,429 | B1 * | 6/2003 | Hallgren | A61B 10/04 128/898 |
| 7,300,632 | B2 * | 11/2007 | Sugiyama | A61B 10/0096 422/50 |
| 9,314,792 | B2 * | 4/2016 | Li | B01L 3/50825 |
| 9,649,061 | B2 * | 5/2017 | Ivosevic | B01L 3/0293 |
| 2001/0008614 | A1 * | 7/2001 | Aronowitz | A61B 10/0051 422/400 |
| 2002/0123697 | A1 * | 9/2002 | Ishizaka | A61B 10/0045 600/572 |
| 2002/0197738 | A1 * | 12/2002 | Matsumoto | A61B 10/0051 436/518 |
| 2003/0028123 | A1 | 2/2003 | Pevoto | |
| 2003/0064526 | A1 * | 4/2003 | Niedbala | A61B 10/0045 436/165 |
| 2004/0022687 | A1 * | 2/2004 | Wuske | A61B 10/0051 422/400 |
| 2004/0267181 | A1 * | 12/2004 | Tuite | A61B 10/02 604/1 |
| 2005/0112547 | A1 * | 5/2005 | Youngkin | C12Q 1/04 435/4 |
| 2006/0018800 | A1 * | 1/2006 | Slowey | A61B 10/02 422/412 |
| 2006/0245977 | A1 * | 11/2006 | Bodner | A61B 10/0045 422/400 |
| 2007/0213632 | A1 * | 9/2007 | Okazaki | A61B 1/012 600/562 |
| 2008/0118397 | A1 * | 5/2008 | Slowey | A61B 10/0051 422/400 |
| 2010/0304359 | A1 * | 12/2010 | Egan | G01N 33/54366 435/5 |
| 2011/0105953 | A1 * | 5/2011 | Lai | A61B 10/0045 600/581 |
| 2011/0159457 | A1 * | 6/2011 | Offermann | A61B 5/417 433/91 |
| 2011/0230737 | A1 | 9/2011 | Duda et al. | |
| 2012/0048130 | A1 * | 3/2012 | Mathew | A47G 21/106 100/297 |
| 2012/0094303 | A1 * | 4/2012 | Engel | A61B 10/0045 435/7.1 |
| 2012/0325721 | A1 * | 12/2012 | Plante | B01L 3/50825 206/577 |
| 2013/0171621 | A1 * | 7/2013 | Luo | C12Q 1/6841 435/5 |
| 2013/0302219 | A1 * | 11/2013 | Li | A61B 10/0051 422/550 |
| 2016/0045187 | A1 * | 2/2016 | Terbrueggen | B01L 3/5023 435/6.1 |
| 2016/0273059 | A1 * | 9/2016 | Benshaul | A61B 10/02 |

OTHER PUBLICATIONS

Adamson et al. "Acceptability and accuracy of Cervical Cancer Screening Using A Self-collected Tampon for HPV Messenger-RNA Testing Among HIV-Infected Women in South Africa", PLoS ONE, 10(9): e0137299-1-e0137299-12, Sep. 2, 2015.

Deny et al. "Women's Perspectives of Self-Sampling for Cervical Screening in South Africa", National Cancer Institute, University of Cape Town, South Africa, Columbia University, New York, USA, Cepheid, Presented at HPV 2017, Cape Town, South Africa, Mar. 4, 2017.

Goodman "HPV Testing as a Screen for Cervical Cancer", TheBMJ, 350: h2372-1-h2372-14, Jun. 30, 2015.

(56) References Cited

OTHER PUBLICATIONS

Rogers et al. "Evaluation of Tampon as a Suitable Self Sampling Device for Detection of HPV mRNA From Cervical Cells—A Preliminary Report", Central European Journal of Public Health, 16(Suppl.): 856-857, Apr. 1, 2008.
Zhao et al. "A Real World Feasibility Study for Using HPV Test as Primary Screening Technology for Cervical Cancer Screening in Rural China", Annals of Global Health, 1(81): 84, # 011TIS032, 2015.
International Preliminary Report on Patentability dated May 6, 2016 From the International Bureau of WIPO Re. Application No. PCT/IL2013/050854.
International Search Report and the Written Opinion dated Dec. 25, 2013 From the International Searching Authority Re. Application No. PCT/IL2013/050854.
Office Action dated Oct. 28, 2019 From the Israel Patent Office Re. Application No. 245163 and Its Translation Into English. (4 Pages).

\* cited by examiner

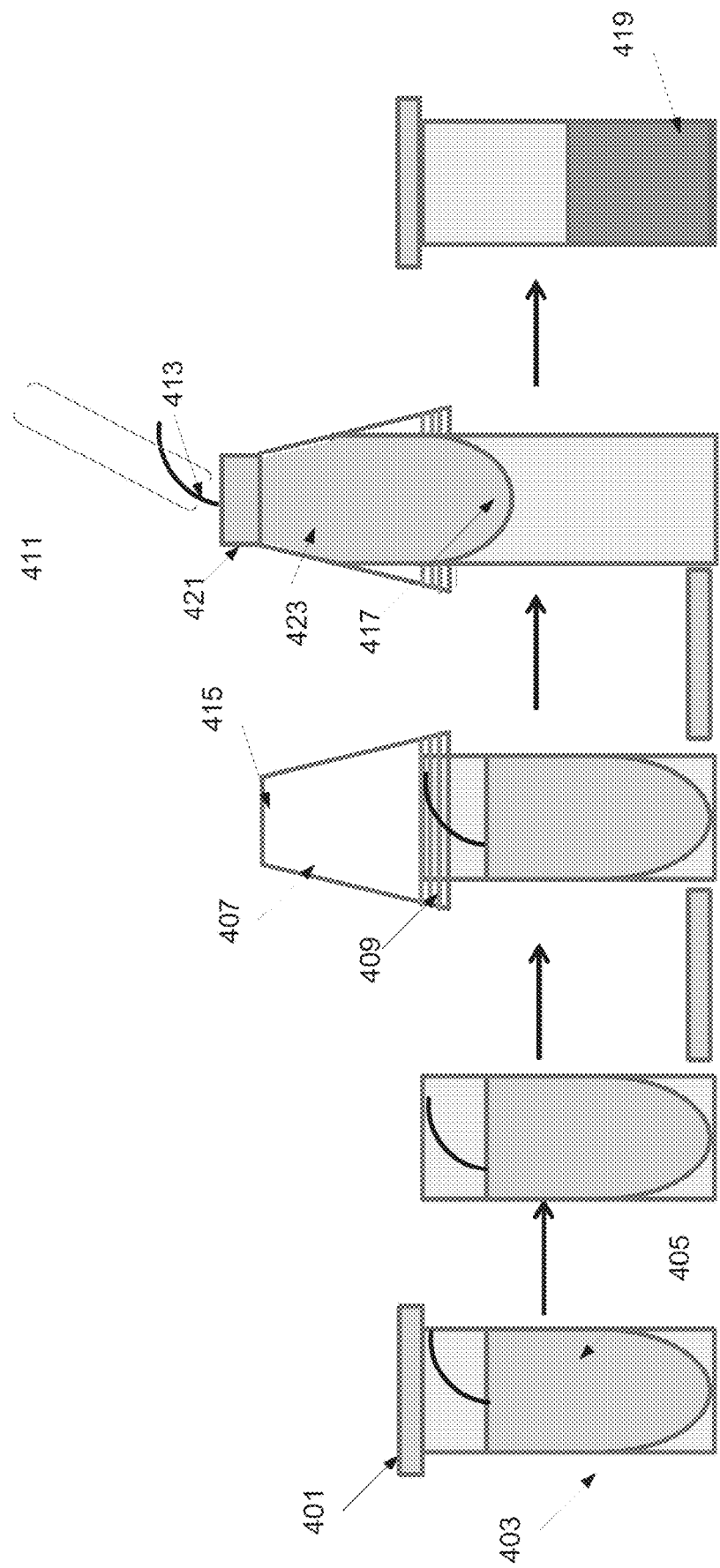

FIG. 8A
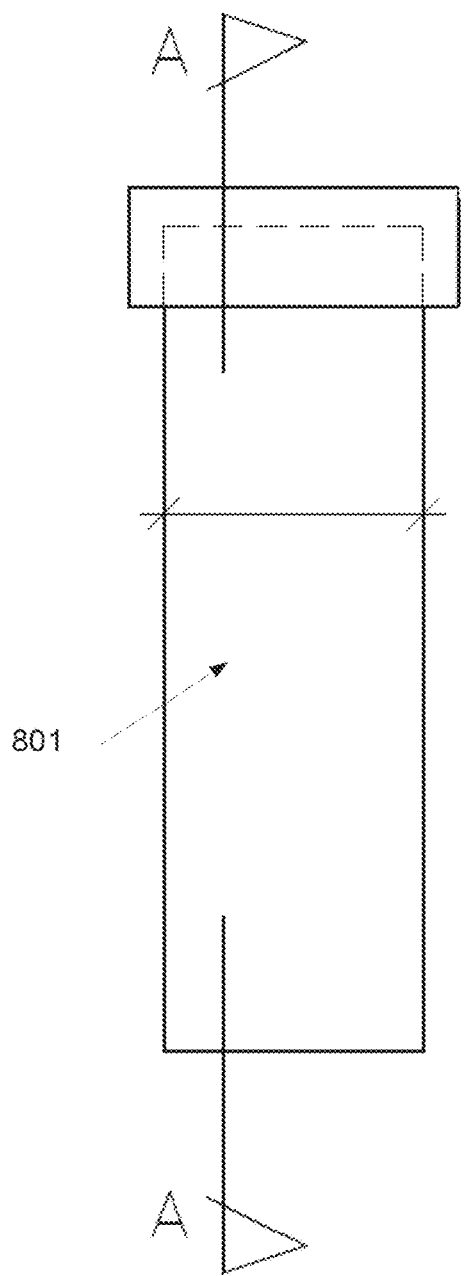
FIG.8B
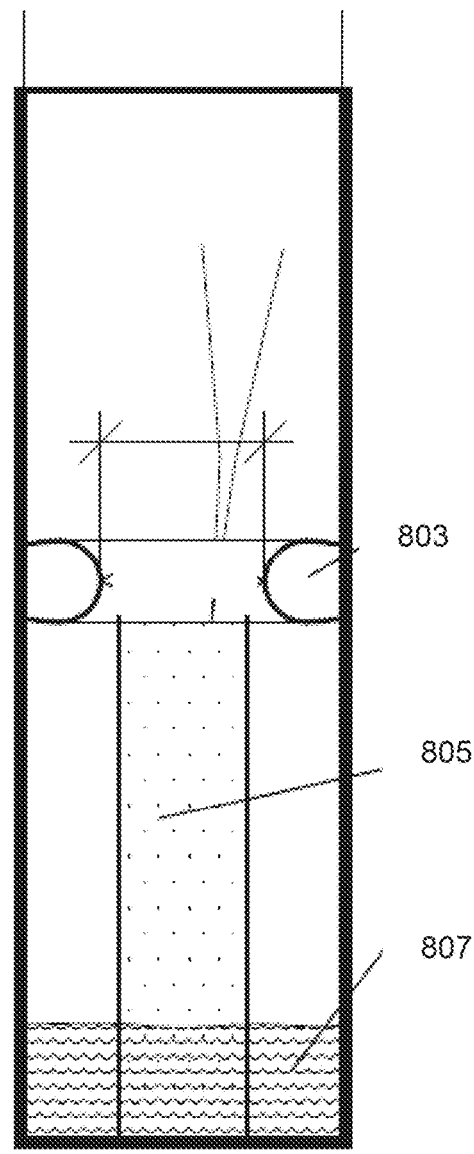
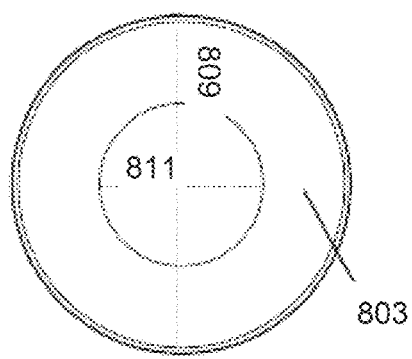
FIG. 8C

KIT AND METHOD FOR COLLECTING BODY FLUID FOR MEDICAL DIAGNOSIS

RELATED APPLICATION

This application is a National Phase of PCT Patent Application No. PCT/IL2013/050854 having International filing date of Oct. 22, 2013. The contents of the above application are all incorporated by reference as if fully set forth herein in their entirety.

FIELD AND BACKGROUND OF THE INVENTION

The present invention, in some embodiments thereof, relates to a kit and/or method of collecting body fluid for medical diagnosis, especially useful in collecting a self collected sample of vaginal fluid and/or cells for nucleic acid testing.

U.S. Pat. No. 6,702,759 to Pevoto discloses "An intra vaginal self-administered cell collecting device and method includes inserting a tampon-like telescoping tube intra-vaginally. The tube includes an expandable preformed absorbent member having a textured cover. The absorbent member also includes a retrieval member extending therefrom. The tube is manipulated to expel the absorbent member intra-vaginally. The tube is removed and the absorbent member is retained intra-vaginally for a period of time. The absorbent member is retained from expanding from its preform when exposed to vaginal fluids by means of a cover on the absorbent material. The cover also captures soughed off cells in the vaginal fluids. The absorbent material is retrieved manually by the retrieval member."

SUMMARY OF THE INVENTION

According to an aspect of some embodiments of the invention there is provided a method for applying a nucleic acid assay comprising collecting body fluid and cells for a nucleic acid assay, and applying a nucleic acid assay to detect pathogenic genomic material, the collecting comprising collecting a sufficient amount of body fluid and cells to improve a sensitivity of the nucleic acid assay by at least 10%. In some embodiments, the collecting comprises extracting fluid and cells from an absorbing member previously inserted into a body orifice. In some embodiments, the pathogenic genomic material comprises at least one of viral genome and bacterial genome. In some embodiments, the viral genome includes at least one of human papillomavirus mRNA and human papillomavirus DNA. In some embodiments, at least one of body fluid and cells are collected from a vagina. In some embodiments, collecting comprises inserting said absorbing member into said body orifice for a time period ranging between 15 minutes to 4 hours. In some embodiments, extracting fluid comprises bursting open cells and releasing their content. In some embodiments, a fluid extraction device is used for extracting fluid and cells. In some embodiments, extracting comprises applying radial pressure on the absorbing member using the fluid extraction device. In some embodiments, extracting comprises applying axial pressure on the absorbing member using the fluid extraction device. In some embodiments, extracting comprises scraping at least a portion of the absorbing member's walls to collect cells using the fluid extraction device. In some embodiments, extracting comprises reducing a size of at least a portion of a swollen absorbing member by passing the absorbing member through an opening of the extraction device. In some embodiments, extracting fluid comprises attaching a fluid extraction device to a sample container. In some embodiments, extracted fluid is collected within the sample container. In some embodiments, extracted fluid blends in a preserving solution within the container, increasing a volume of the liquid.

According to an aspect of some embodiments of the invention there is provided a kit for collecting a body fluid sample, comprising: an absorbing member, a sample container, and a shipping box, the sample container comprising a buffer solution for preserving a collected sample. In some embodiments, the kit is a home-use kit, and the sample is self collected by a user.

According to an aspect of some embodiments of the invention there is provided a fluid extraction device for collecting fluid from an absorbing member, the device comprising at least one opening defining an aperture small enough to squeeze the absorbing member as it is passed through the aperture for extracting fluid from the absorbing member, the device attachable to a sample container. In some embodiments, the fluid extraction device is sized to fit on top of a sample container. In some embodiments, the device comprises a threaded opening for attaching the device to the sample container. In some embodiments, the fluid extraction device comprises at least one curvature for channeling extracted fluid into a sample container.

According to an aspect of some embodiments of the invention there is provided a fluid extraction device for collecting fluid from an absorbing member, comprising a barrel having a diameter at least as long as a diameter of the absorbing member when the absorbing member is expanded, and a plunger for squeezing the absorbing member to extract fluid, the barrel comprising an opening smaller than an opening of a sample container.

According to an aspect of some embodiments of the invention there is provided a method for extracting fluid using a fluid extraction device, comprising passing an absorbing member through an aperture of a fluid extraction device, the aperture small enough to squeeze said absorbing member as it is passed through, and collecting extracted fluid which accumulates on at least one wall of the fluid extraction device.

According to an aspect of some embodiments of the invention there is provided a sample container comprising an extracting element, the extracting element forming a passage within the container having an aperture small enough to squeeze an absorbing member as it is passed through for extracting fluid from the absorbing member. In some embodiments, the extracting element is shaped as an "o-ring" circumferentially mounted on the walls of the container. In some embodiments, a plurality of extracting elements are arranged within the sample container so that they form a passage which gradually decreases in diameter, for applying increased pressure onto the walls of the absorbing member as it is passed through. In some embodiments, the extracting element is a curve of a wall of said container, forming an internally facing bulge within the container.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 4A-E are a set of illustrations describing a method for collecting fluid that is captured in an absorbing member using a funnel shaped fluid extraction device, according to some embodiments of the invention;

FIGS. 8A-C are drawings of a sample container comprising an extracting element for extracting fluid from an absorbing member, according to some embodiments of the invention;

DESCRIPTION OF SPECIFIC EMBODIMENTS OF THE INVENTION

Figure 1A:
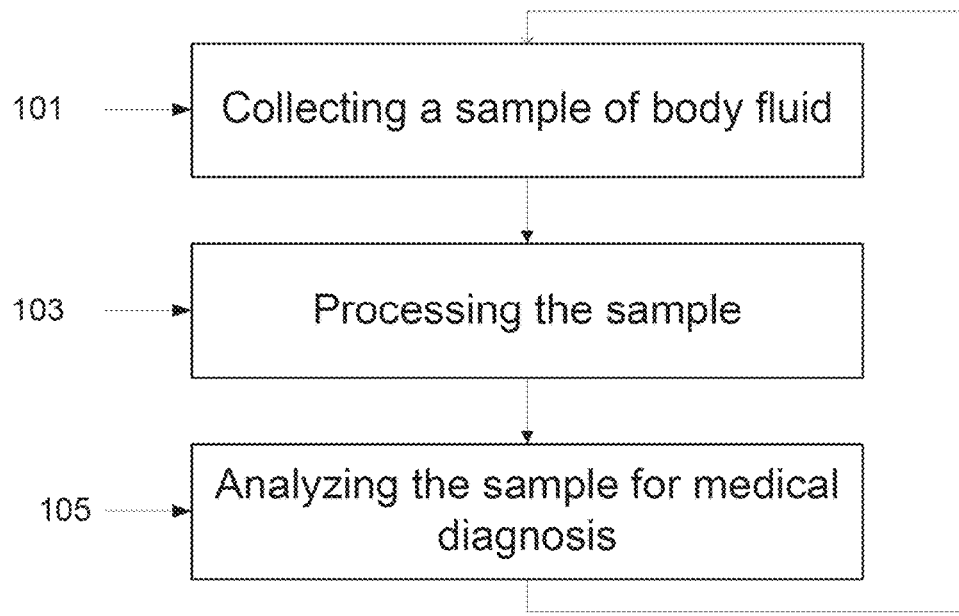
FIGS. 1A-B are flowcharts of a general method of collecting body fluid and cells for medical diagnosis, according to some embodiments of the invention.

The present invention, in some embodiments thereof, relates to a kit and/or method of collecting body fluid for medical diagnosis. A particular feature of some embodiments includes collecting fluid which may contain nucleic acid from cells, for example from cells that are damaged or are burst open.

According to an aspect of some embodiments of the invention, the method comprises extracting fluid from a sample collected from a human body orifice. In some embodiments, the fluid comprises cells.

In some embodiments, a sample is collected by inserting an absorbing member into a body orifice, such as the vagina or the anus, for a period of time long enough to collect a sufficient amount of bodily fluid, such as 1 hour, 1.5 hours, 2 hours, 3 hours, 5 hours, or any intermediate, longer or shorter time periods. In some embodiments, the sample is retrieved from the orifice and is placed in a container for further processing and analysis. In some embodiments, the absorbing member and/or container are a part of a kit. In some embodiments, the kit is a home use kit. Optionally, the sample is self collected by the patient.

In some embodiments, the collected sample is processed. In some embodiments, processing is performed in a laboratory. In some embodiments, processing the sample includes extracting fluid that was absorbed by the absorbing member. In some embodiments, processing the sample includes extracting cells that were absorbed by the absorbing member and/or cells collected on the absorbing member's walls. In some embodiments, a fluid extraction device is used for extracting the fluid and/or the cells. Optionally, if the fluid comprises cells, the fluid extraction process may cause the cells to burst open, and cell content is released. In some embodiments, the extracted fluid is collected within the original sample container.

In some embodiments, the extracted fluid and/or cells are tested, for example tested for the presence of pathogenic genomic, such as viral and/or bacterial genome. In some embodiments, testing includes nucleic acid testing procedures. In one example, fluid collected from a vagina is tested for the presence of Human Papillomavirus, for example by testing the presence of human papillomavirus mRNA and/or human papillomavirus DNA. A potential advantage of testing both fluid and cell content includes improving a sensitivity of the test. Optionally, collecting fluid and cells increases the amount of the collected genetic material.

An aspect of some embodiments of the invention relates to a fluid extraction device. In some embodiments, the fluid extraction device comprises at least one opening small enough to squeeze the absorbing member as it is passed through. In some embodiments, at least a portion of the fluid extraction device is used for applying pressure on the absorbing member, to cause fluid and/or cells to flow out. In some embodiments, the fluid extraction device is adapted for scraping a surface of the absorbing member, for example to collect cells that adhered to the walls. In some embodiments, the fluid extraction device is assembled onto the sample container.

The fluid extraction device may be shaped in various configurations. For example, in some embodiments, the fluid extraction device is a funnel shaped device. In some embodiments, the fluid extraction device is shaped as forceps. In some embodiments, the fluid extraction device is a syringe-like device, comprising a barrel and a plunger.

In some embodiments, the fluid extraction device is mechanically activated by a user, for example a laboratory technician. In some embodiments, the device is disposable, and may be discarded along with the absorbing member at the end of the fluid extraction process. In some embodiments, the fluid extraction device comprises a mechanism for trapping the absorbing member within it.

In some embodiments, a sample container in which the absorbing member is retained comprises one or more extracting element for collecting fluid from the absorbing member. Optionally, the extracting element forms a passage within the container having an aperture small enough to squeeze the absorbing member as it is pulled through the container, for collecting fluid. In some embodiments, the extracting member is attached to the container, for example circumferentially mounted to the container walls. In some embodiments, a plurality of extracting elements are used, optionally forming a passage in which increased pressure is gradually applied on the absorbing member to extract fluid.

In some embodiments, the sample container comprises a narrowing, for example forming a bottle shaped container with a neck, for squeezing the absorbing member as it is passed through during removal and/or insertion of the absorbing member.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

General Description

Referring now to the drawings, FIG. 1A is a flowchart of a method for collecting body fluid for medical diagnosis, according to some embodiments of the invention.

In some embodiments, a sample of fluid is collected from the human body (101). Optionally, the fluid comprises cells. In some embodiments, the sample is collected by inserting an absorbing member, such as a tampon, into a body orifice, for example the vagina, anus, and/or any other orifices of the body. In some embodiments, the absorbing member is a component of a home use kit, and the sample is self collected by a patient.

In some embodiments, the absorbing member is inserted into the body orifice for a predefined period of time, for example 1 hour, 2 hours, 15 minutes, 30 minutes, 3 hours, 4 hours, or any intermediate, shorter or longer time periods. Optionally, fluid such as vaginal fluid is absorbed by the absorbing member. Optionally, cells are absorbed by the absorbing member, and/or adhere to the walls of the absorbing member. In some embodiments, once the absorbing member is retrieved from the body orifice, it is placed in a sealable container. In some embodiments, the container comprises a solution for preserving the collected sample, such as PBS solution. In some embodiments, the container with the collected sample is transferred to a laboratory, for example by shipping.

In some embodiments, the collected sample is processed (103). Optionally, processing comprises extracting the collected liquid (and/or cells) from the absorbing member, for example by applying pressure onto the absorbing member (e.g. by squeezing), to cause the fluid and/or cells to flow out.

In some embodiments, a designated fluid extraction device is used for extracting the fluid. The device may be configured for connecting to a cap of the container, and/or configured for positioning on top of an open container, so that fluid and cells collected from the absorbing member flow directly into the container. In some embodiments, the extracted fluid and/or cells are collected in the original sample container. Following the fluid extraction process, the absorbing member and/or the extraction device may be discarded.

In some embodiments, the sample is analyzed for medical diagnosis purposes (105). In some embodiments, the analysis method is selected according to the orifice from which the fluid and/or cells were collected, and/or according to type of diseases that are tested. In some embodiments, testing includes applying nucleic acid testing procedures. In some embodiments, the sample is tested for the presence of pathogenic genetic material. For example, fluid and/or cells that were collected from a vagina may be tested for one or more of the following: human papillomavirus (HPV), *Chlamydia trachomatis*, *Neisseria gonorrhoea*, *Trichomonas vaginalis*, and/or *Mycoplasma genitalium*. In one example, nucleic acid testing comprises testing for human papillomavirus mRNA and/or human papillomavirus DNA. In another example, fluid and/or cells collected from the anus are tested for the presence of HPV. In some cases, presence of HPV in the anal canal may be linked with anal cancer.

In some embodiments, at least a portion of the method described at FIG. 1A is repeated. Optionally, repeating the method includes collecting a second sample from the same body orifice. Optionally, repeating the method includes collecting a second sample from a different body orifice.

Figure 1B:
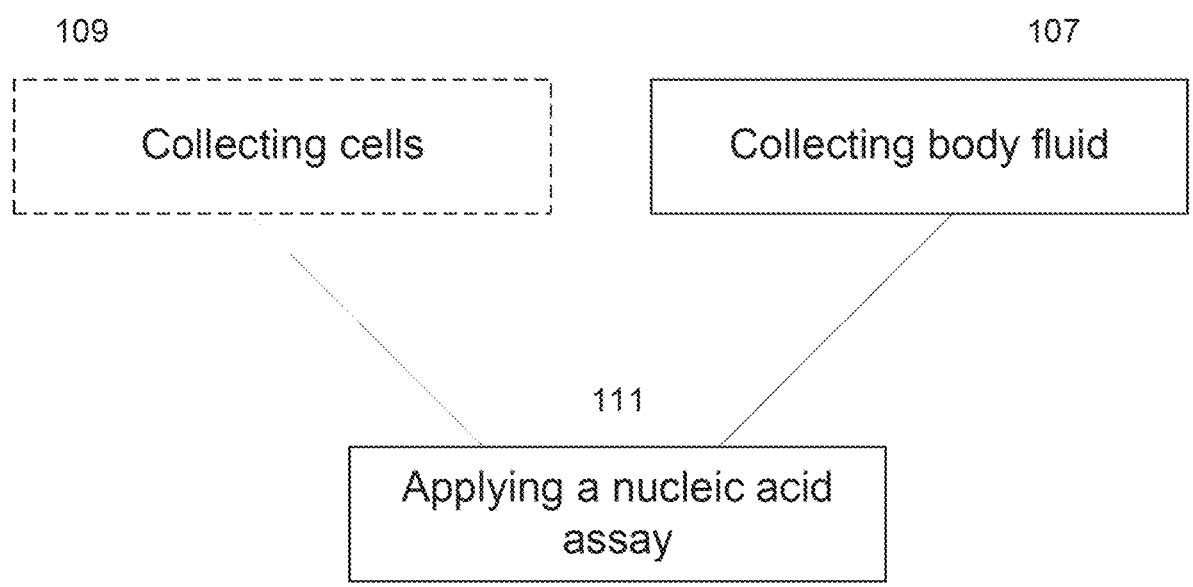

FIG. 1B is a schematic flowchart of a method for applying a nucleic acid assay. In some embodiments, body fluid is collected 107. Optionally, cells are collected 109, for example cells that exist within the body fluid and/or cells collected by an absorbing member by contacting tissue, for example cells that adhere to the walls of the absorbing member. An amount of collected fluid, according to some embodiments, needs to be sufficient for applying a reliable assay to test the fluid, for example applying a nucleic acid assay 111 to test, for example, for HPV mRNA and/or HPV DNA.

Description of an Exemplary Method for Collecting a Body Fluid Sample

Figure 2:
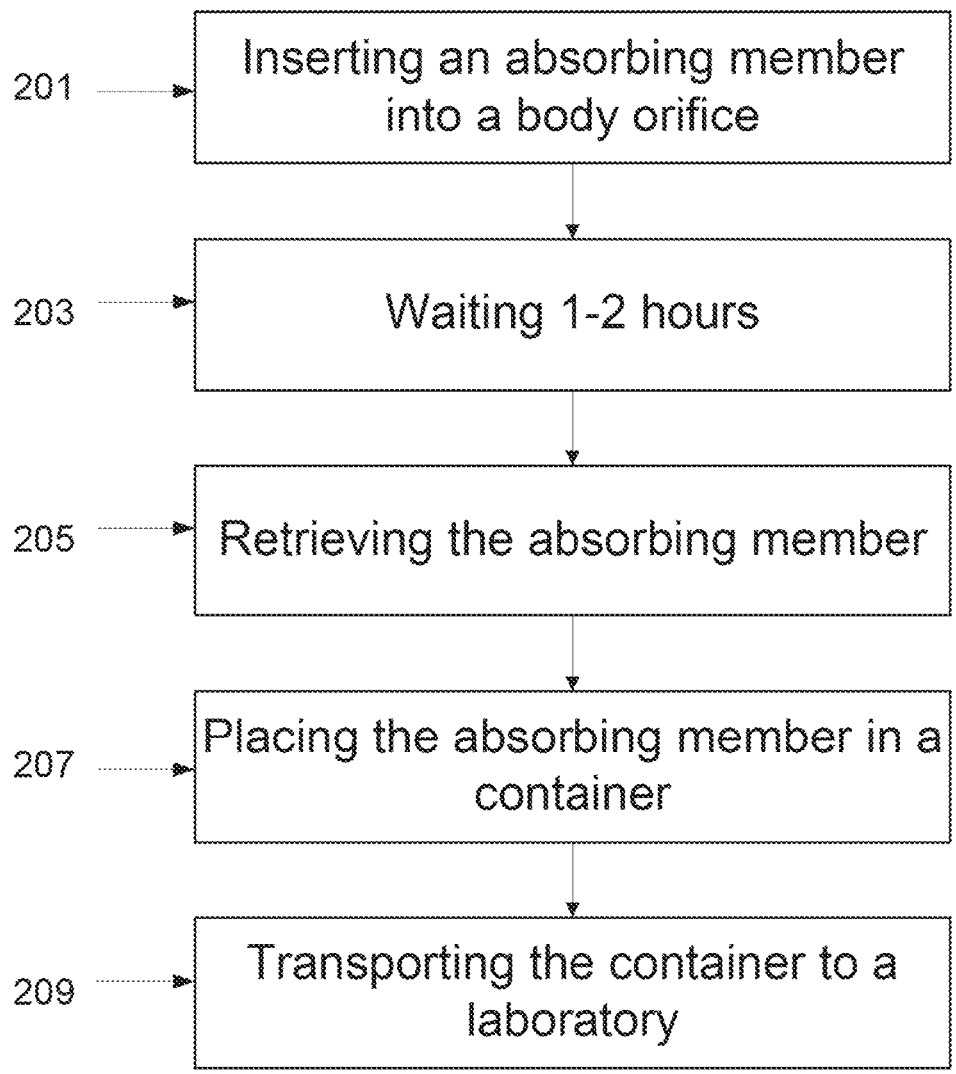
FIG. 2 is a flowchart of an exemplary method for collecting a sample of body fluid by using an absorbing member, according to some embodiments of the invention.

FIG. 2 is a flowchart of an exemplary method for collecting a sample of body fluid using an absorbing member, according to some embodiments of the invention. In some embodiments, a kit comprising an absorbing member, a container, and optionally a shipping box is used for the collection of body fluid.

In some embodiments, an absorbing member is inserted into a body orifice (201), for example a patient may insert the absorbing member into a vagina using a commonly known tampon insertion method.

In some embodiments, the patient inserts the absorbing member directly into the orifice, for example with a proximal end of the absorbing member entering first. In some embodiments, an applicator may be used to facilitate insertion of the absorbing member into an orifice.

In some embodiments, an absorbing member includes a sponge having a shape and size suitable for insertion into a body orifice, for example having a cylindrical shape. In one example, the absorbing member is a standard tampon. In some embodiments, the absorbing member is made of a sponge material, such as rayon and/or cotton.

In some embodiments, the absorbing member comprises an attached cord. Optionally, the cord is connected to a distal end of the absorbing member. In some embodiments, at least a portion of the attached cord remains externally to the body when the absorbing member is inserted into the orifice.

In some embodiments, a body orifice is an opening, from which body fluid can be collected, for example the vagina or anus. In some embodiments, a body fluid includes a liquid which was secreted and/or excreted from organs, for example vaginal fluid or anal fluid.

In some embodiments, the absorbing member is positioned within the orifice for a predefined period of time (203), for example 1 hour, 1.5 hours, 2 hours, 2.5 hours, and/or any intermediate or smaller time periods. Optionally, the time period is determined according to the orifice from which the fluid is collected, setting a duration long enough to collect a sufficient amount of fluid for further analysis.

In some embodiments, the absorbing member swells as the fluid accumulates. Optionally, the absorbing member expands, for example expands axially and/or radially. It is possible that fluid is drawn to a center of the absorbing member, for example due to gravity. In some embodiments, the collected fluid comprises cells, such as tissue cells.

Additionally or alternatively, cells adhere to the external walls of the absorbing member, for example due to direct contact between the absorbing member and surrounding tissue, such as vaginal tissue. Optionally, cells are collected by the absorbing member during insertion to the body orifice, and/or during removal from the body orifice. In some embodiments, cells are collected as the absorbing member rubs against a surface of the tissue. Optionally, a portion of the absorbing member scratches a surface of the tissue, scraping off cells from the tissue.

In some embodiments, after a certain time period, for example a predefined time period such as 2 hours, the absorbing member is retrieved from the body orifice (203) by the user. In some embodiments, the absorbing member is retrieved by tugging the portion of the cord that remained outside the orifice. An attachment between the cord and the absorbing member has to be strong enough to prevent tear off of the cord. Optionally, tear off is prevented by using a cord material that is tear resistant. Additionally or alternatively, tear off is prevented by using an attachment type that is less likely to tear off, for example at least a portion of the cord may be sewn along at least a portion of the absorbing member.

In some embodiments, once the absorbing member is retrieved from the orifice, it is placed in a container (207). Optionally, the absorbing member is positioned in the container with the cord facing upwards in direction of the container opening. As this direction complies with the direction of removal from the body orifice, a user may retrieve the absorbing member from the orifice and insert it into the container in a single motion. In some embodiments, a cap of the container is unscrewed during insertion of the sample into the container, and screwed again to seal the container after insertion.

In some embodiments, the container comprises a solution for preserving the collected sample, for example a buffer solution such as PBS (phosphate buffered saline) solution. In some embodiments, the sample can be preserved in the container for a period of time, for example up to 3 months. Optionally, the sample is preserved for a longer period of time, for example 1 year, by maintaining it in cool temperature conditions ranging between −20° C. to −70° C. In some embodiments, the absorbing member soaks at least a portion of the preserving solution as it is kept within container.

In some embodiments, the sealed container is placed in a shipping box, which can be transported for further processing and analysis in a laboratory (209). Optionally, the shipping box includes a designated compartment and/or softening packaging material to prevent damage such as breakage to the sealed container. In some embodiments, the sealed container is transferred to a laboratory using other means, for example the patient may hand the sample directly to a laboratory.

Description of an Exemplary Method for Processing a Body Fluid Sample

Figure 3:
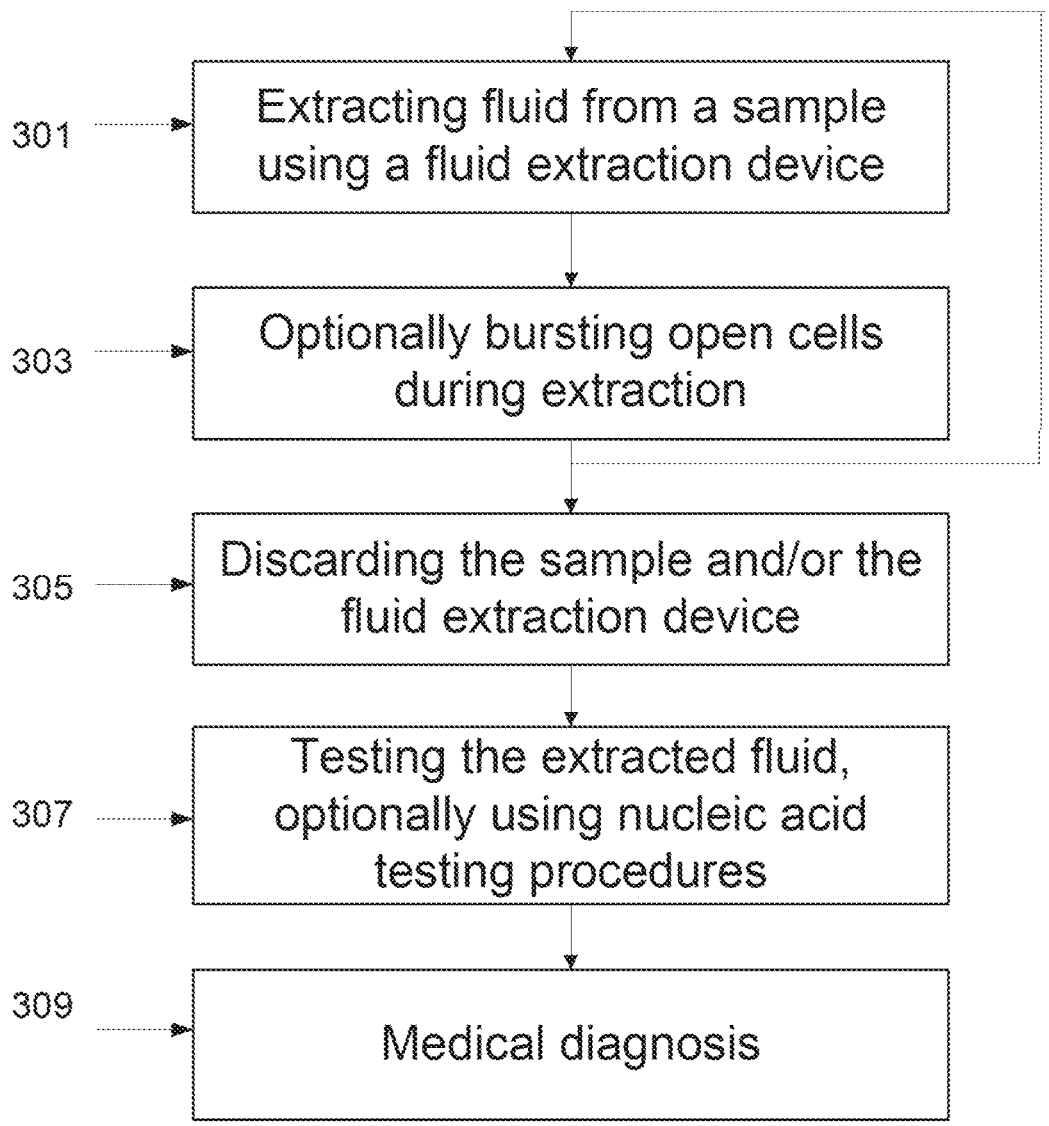
FIG. 3 is a flowchart of a method for processing and further analyzing a sample of body fluid, according to some embodiments of the invention.

FIG. 3 is a flowchart of a method for processing and further analyzing a sample of body fluid, according to some embodiments of the invention. In some embodiments, as previously described, a container with a collected sample arrives at a laboratory. In some embodiments, the collected body fluid is extracted from the absorbing member using a fluid extraction device (301).

In some embodiments, the container is unsealed, for example by removing the cap, and the fluid extraction device is positioned over the opening. Alternatively, the cap of the container remains sealed, and a hole may be pierced through the cap to allow pulling the absorbing member towards the fluid extraction device through the hole. Additionally or alternatively, at least a portion of the fluid extraction device is inserted into the container.

In some embodiments, a fluid extraction device is adapted for applying pressure onto at least a portion of the absorbing member. In some embodiments, the absorbing member is pulled through the fluid extraction device, for example through a funnel shaped device. In some embodiments, the absorbing member is captured by the fluid extraction device, for example in a barrel of a syringe like device, and a plunger is used for applying pressure, for example from a distal end towards a proximal end of the absorbing member. In some embodiments, the fluid extraction device clasps onto the absorbing member in a tweezer-like manner, for applying pressure on opposite sides of the absorbing member.

In some embodiments, the fluid extraction device comprises an opening which is small enough to squeeze the absorbing member as it is pulled through, and yet large enough to allow the passing the absorbing member through.

In some embodiments, a user, for example a laboratory technician, activates the fluid extraction device. In some embodiments, the absorbing member is pulled through one or more openings of the device by grasping the absorbing member's cord. Optionally, the preserving solution in the container provides a wet environment, in which the cord does not stick to the absorbing member, and can be easily grasped.

In some embodiments, at least a portion of the device channels the extracted fluid into the container, for example the portion may have a curvature which causes the extracted fluid to flow into the container. Optionally, at least a portion of the device is made and/or coated with a material smooth enough so that fluid that hits the walls of the device flows directly into the container.

In some embodiments, during the extraction process, cells that are found within the fluid or, for example, on the external walls of the absorbing member, are burst open (303). Additionally or alternatively, a lysis solution can be added to burst open cells. Optionally, intracellular fluid is released, and flows into the container. The intracellular fluid may comprise genome material, such as viral genome.

In one example, basal cells of epithelial tissue, for example vaginal tissue, are collected by the absorbing member. Optionally, the basal cells are infected by HPV virion, and contain viral genome, for example in the cell nucleus. Optionally, since HPV is a non-lytic virus, a cell that contains the virus remains whole before the extraction procedure. In some embodiments, during the extraction process the cells are burst open, for example due to the applied pressure on the absorbing member. The released intracellular fluid may contain viral genome.

In some embodiments, the fluid extraction process is repeated, for example to extract additional fluid into the container. Optionally, the extraction process is repeated one, two, three or four times, or until a sufficient amount of fluid is extracted.

In some embodiments, the extracted fluid mixes with the preserving solution that was previously inside the container. Optionally, this increases a volume of the fluid.

In some embodiments, at the end of the extraction process, the device and/or the absorbing member are discarded (305).

In some embodiments, the extracted fluid is tested (307). In some embodiments, testing includes nucleic acid testing procedures. Optionally, nucleic acid testing includes applying a polymerase chain reaction (PCR) and/or a reverse transcription polymerase chain reaction (RT-PCR) process. In one example, RT-PCR is applied to detect HPV mRNA E6/E7. HPV mRNA E6/E7 may be found in the collected vaginal fluid and/or in the collected cells.

Other examples of nucleic acid methods for testing the extracted fluid include transcription mediated amplification, branched DNA tests, and/or ligase chain reaction (LCR) methods.

A potential advantage of testing fluid and/or cells (which may or may not have been burst open) includes improving the sensitivity of the test, for example because an increased amount of genetic material may be collected in comparison to, for example, genetic material collected from cells only. In some embodiments, sensitivity of the test is improved by, for example, 10% 30%, 50% 70% or any other intermediate, higher or lower values.

In some embodiments, a diagnostic decision is made according to the testing results (309). In some embodiments, the presence of a virus and/or a bacterium is detected. For example, the presence of HPV is detected. Optionally, high-risk HPV is detected. Infection caused by high risk HPV may be linked with cervical, vaginal, or anal cancer.

In some embodiments, the patient and/or a physician and/or other medical facility are informed with the diagnostic decision. Optionally, a method of treatment is decided according to the diagnostic decision.

FIGS. 4A-E are a set of illustrations describing a method for collecting fluid that is captured in an absorbing member using a funnel shaped fluid extraction device, according to some embodiments of the invention.

A funnel shaped fluid extraction device, as described in some embodiments of the invention, may include a device comprising a narrowing and a widening, for example a cone shaped device, and/or a device comprising at least one aperture small enough to squeeze an absorbing member. In some embodiments, the device comprises an aperture large enough to remove the absorbing member.

In some embodiments, as shown in FIGS. 4A and 4B, a cap 401 is removed from a container 403, in which absorbing member 405 was previously placed. Alternatively, cap 401 is a piercable cap, and a hole is punctured in it. In some embodiments, cap 401 comprises a slot through which cord 413 may be threaded. Optionally, cord 413 is long enough so that during removal of cap 401, absorbing member remains within container 403.

A funnel shaped fluid extraction device 407, as shown at 4C, is positioned on a rim of container 403. In some embodiments, a circumferential edge at the wider opening of device 407 comprises a thread 409 for threading device 407 onto the container's rim. In some embodiments, device 407 is positioned on top of a piercable cap.

In some embodiments, as shown at 4D, a user pulls absorbing member 405 from container 403 through device 407 to extract fluid from the absorbing member into the container. Optionally, tweezers 411 are used for grasping cord 413, which is attached to a distal end of absorbing member 405, to pull the absorbing member through device 407. Alternatively, tweezers 411 are used for grasping the main body of absorbing member 405, for example at a distal portion.

In some embodiments, device 407 has at least one opening 415 defining an aperture small enough to squeeze absorbing member 405 as it is passed through the opening. Optionally, a diameter of opening 415 is shorter than a diameter of expanded absorbing member 405, for example 1 mm, 0.5 mm, 2 mm shorter. Efficient fluid extraction may depend on the size and/or shape of the narrowest opening of device, such as opening 415.

When absorbing member 405 is pulled through, at least a portion of it 421 narrows in diameter as it passes through opening 415, while a different portion such as portion 423 remains in the expanded position until being squeezed by the walls of device 407.

In some embodiments, absorbing member 405 is pulled through opening 415 so that it fully exits device 407. In some embodiments, the user prevents from the proximal end 417 of absorbing member 405 is to exit opening 415 of the device, for example allowing the device to trap the absorbing member.

In some embodiments, the user removes device 407 from container 403, for example by unscrewing it, and discards device 407 and/or absorbing member 405 that is trapped within it. Alternatively, absorbing member 405 and device 407 are disposed of separately.

FIG. 4E shows container 403 comprising fluid 419 that was extracted from absorbing member 405, and/or preserving solution. In some embodiments, cap 401 is placed back on container 403.

FIGS. 5A-D are a schematic drawing (5A) and various embodiments (5B-5D) of a fluid extraction device, according to some embodiments of the invention.

Figure 5A:
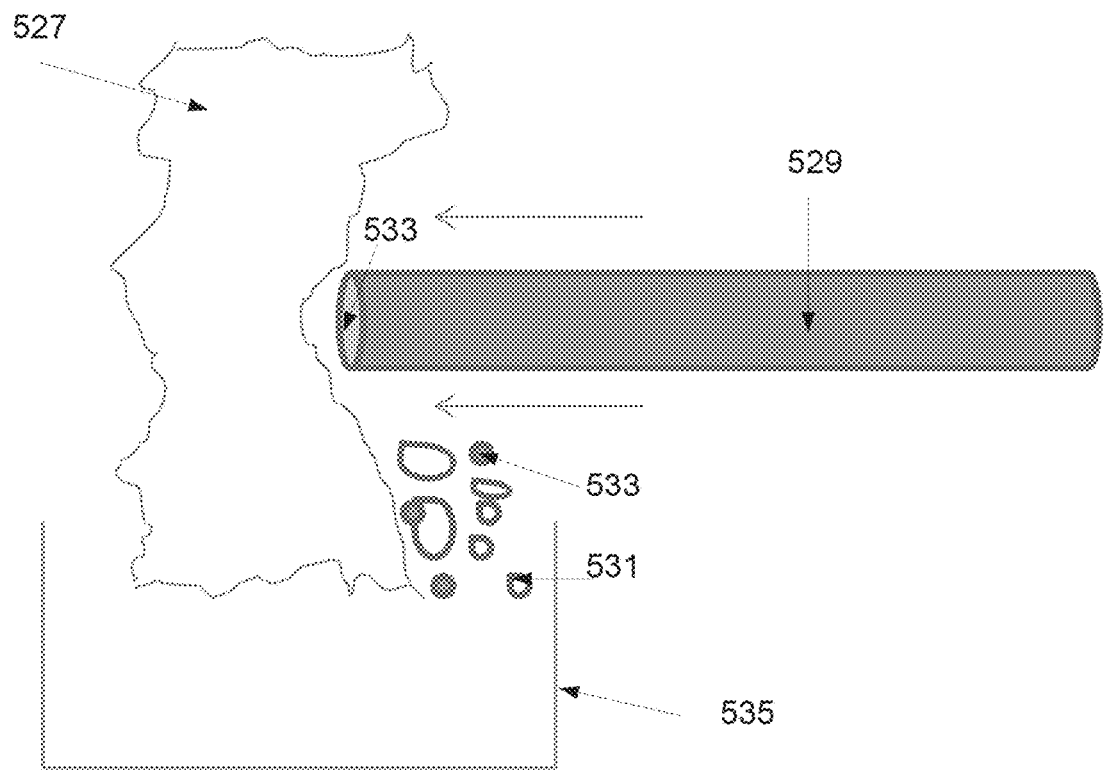
FIGS. 5A-D are a schematic drawing and various embodiments of a fluid extraction device, according to some embodiments of the invention.

FIG. 5A is a schematic drawing showing an absorbing member 527 that has been soaked by body fluid and/or cells. In some embodiments, a fluid extraction device, schematically shown as 529, is used for applying pressure onto absorbing member 527 to cause fluid 531 and/or cells 531 to flow out from absorbing member 527. In some embodiments, radial pressure is applied onto the absorbing member. Additionally or alternatively, axial pressure is applied onto the absorbing member. Additional and/or alternatively, pressure is applied to any surface and/or from any direction onto the absorbing member, to cause fluid and/or cells to flow out. Optionally, fluid 531 and/or cells are collected within a container 535. In some embodiments, at least a portion of device 529, such as portion 537, contacts a surface of the absorbing member wall. Optionally, contact involves scraping of the absorbing member wall to collect cells.

Figure 5B:
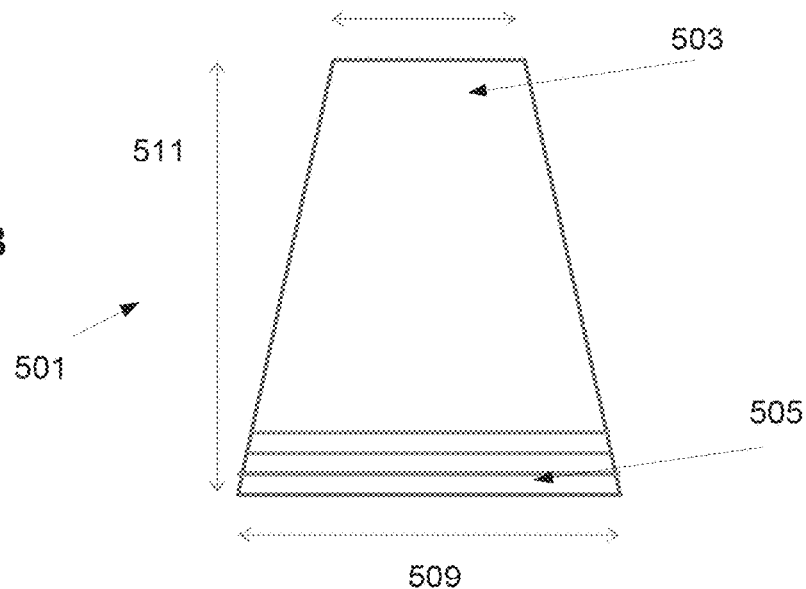

FIG. 5B shows a funnel shaped fluid extraction device 501. In some embodiments, a narrow opening 503 of the device is small enough to squeeze an absorbing member as it is passed through, for example having a diameter 507 ranging between 8-15 mm, such as 9 mm, 12.5 mm, 14 mm. In some embodiments, a wide opening 505 of the device is sized according to a size of the container opening, for example having a diameter 509 ranging between 20-35 mm, such as 22 mm, 25 mm, 32 mm. In some embodiments, a height 511 of device 501 ranges between 25-50 mm, for example 30 mm, 40 mm, 47 mm. In some embodiments, height 511 is short enough so that a user can grasp onto a cord of the absorbing member, that is located within the container, for example by inserting tweezers through openings 503 and 505. Optionally, height 511 is long enough to allow lifting the absorbing member above a surface of the solution within the container.

In some embodiments, device 501 is made of a disposable material, such as plastic. In some embodiments, device 501 is made of a transparent material, for example to facilitate visualizing the cord by a user. In some embodiments, opening 503 comprises an element for preventing splashing of fluid externally to device 501 during extraction, for example an element shaped as a shorter funnel having an opposite orientation from the larger funnel, providing a circumferential wall for preventing splashing.

Figure 5C:
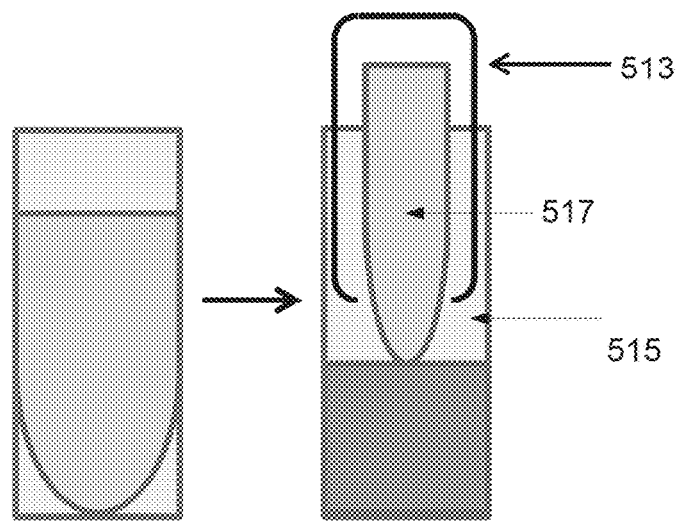

FIG. 5C shows a forceps fluid extraction device 513, according to some embodiments of the invention. In some embodiments, device 513 is narrow enough to be inserted into container 515. Optionally, a user grasps absorbing member 517 using forceps 513, optionally raises the absorbing member above a surface of solution 519, and applies pressure onto opposite sides of absorbing member 517 by applying manual force on forceps 513. In some embodiments, forceps 513 comprise an additional hand piece for facilitating grasping absorbing member 517.

Figure 5D:
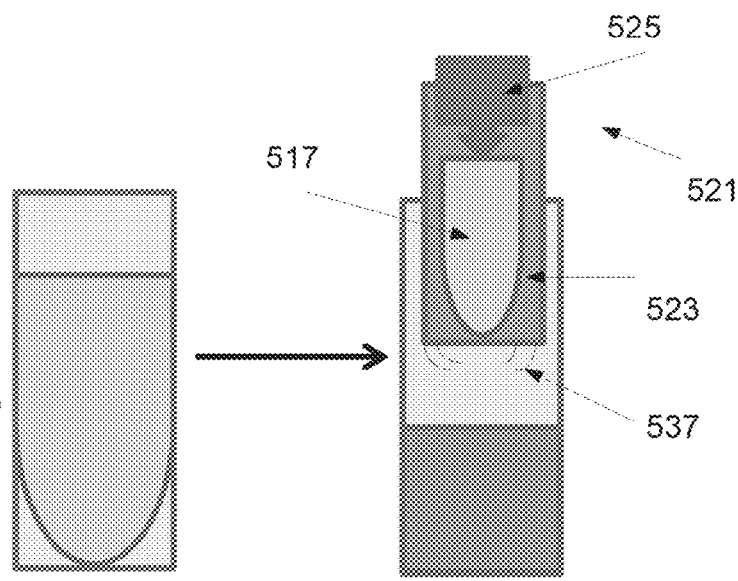

FIG. 5D shows a syringe-like fluid extraction device 521. In some embodiments, device 521 comprises a barrel 523 and a plunger 525. In some embodiments, a diameter of barrel 523 is larger than a diameter of swollen absorbing member 517, and smaller than a diameter of container 515 so that at least a portion of barrel 515 can be inserted into container 515. In some embodiments, plunger 525 is inserted to container 515 when it is pushed to a lowest position within barrel 523. In some embodiments, plunger 525 comprises grasping elements, such as hooks 537, to grasp absorbing member 517. Optionally, a user mechanically controls a position of the hooks from an open position to a closed position. In some embodiments, once absorbing member 517 is grasped by plunger 525, the plunger is pulled up through barrel 523 by the user, to locate absorbing member 517 within barrel 523. In some embodiments, a user pushes plunger 525 to squeeze absorbing member 517 from a distal end towards a proximal end for extracting fluid. In some embodiments, absorbing member is pushed against hooks 537 when they are in a closed position, and the axial pressure applied by plunger 525 causes fluid and/or cells to flow out of the absorbing member, in between hooks 537 into the container. Other embodiments may include a colander like surface, a meshed surface or any other surface positionable at the lower end of barrel 523, allowing flow of liquid through, in which absorbing member 517 can be pushed against.

Figure 6:
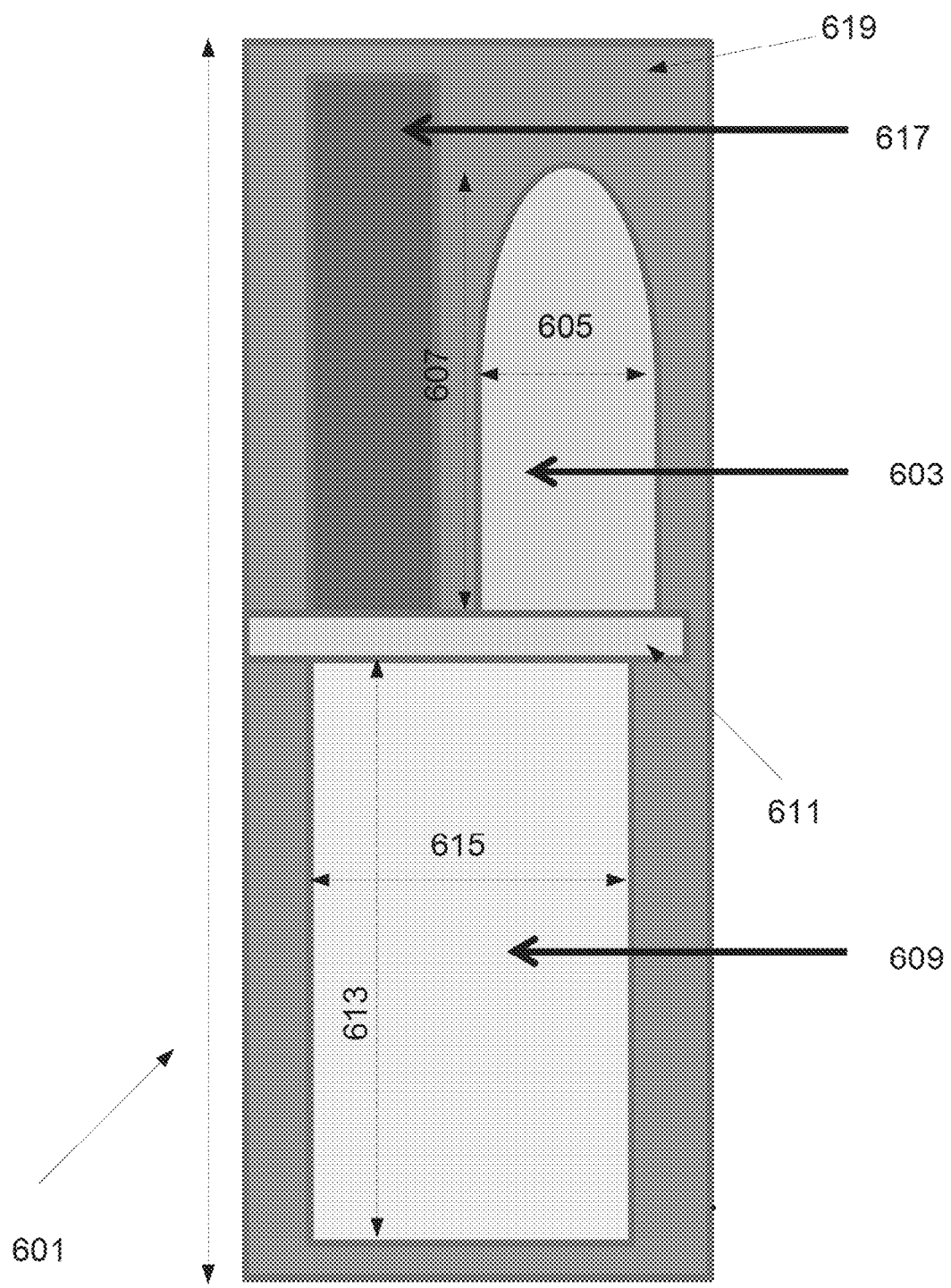
FIG. 6 is a schematic illustration of a kit for collecting body fluid, according to some embodiments of the invention.

FIG. 6 is a schematic illustration of a kit 601 for collecting body fluid, according to some embodiments of the invention. In some embodiments, kit 601 is a home use kit, and the sample is self collected by a patient.

In some embodiments, kit 601 comprises an absorbing member 603. In some embodiments, absorbing member 603 is cylindrical. In some embodiments, absorbing member 603 is conical. In some embodiments, absorbing member 603 has a narrow tip, optionally pointy, for example to facilitate insertion into the body orifice. In some embodiments, dimensions of the absorbing member in its pre-soaked condition include a diameter 605 ranging between 6-15 mm, and a height 607 ranging between 30-55 mm. Exemplary dimensions of absorbing member 603 in its pre-soaked condition include a diameter 605 of 11 mm, and a height 607 of 45 mm. The absorbing member may expand to, for example, a diameter ranging between 12-30 mm, such as 25 mm.

In some embodiments, kit 601 comprises a container 609, sealed with a cap 611. In some embodiments, container 609 contains a preserving solution (not shown in this figure), for example comprising 3-15 ml of PBS solution. In some embodiments, container 609 is large enough to accommodate a swollen absorbing member 603. In some embodiments, dimensions of the container include a height ranging between 40-120 mm, and a diameter ranging between 7-30 mm. Exemplary dimensions of container 609 are a height 613 of 88 mm, and a diameter 615 of 25 mm. In some embodiments, container 609 (and/or cap 611) is made of a transparent and/or non-breakable and/or disposable material, such as plastic. A container may be shaped in other forms, such as cuboids.

In some embodiments, kit 601 comprises instructions for use 617.

In some embodiments, kit 601 is packed inside a box 619, for example being a cardboard box. In some embodiments, the dimensions of the box comply with dimensions of the kit components. Exemplary dimensions of the box, corresponding with the above exemplary dimension of the components, are a height 621 of 125 mm, a width 623 of 35 mm, and a depth of 35 mm.

In some embodiments, cap 611 may be used as the fluid extraction device, for example being shaped as a funnel shaped cap having a sealing such as a foil sealing covering the narrow opening of the funnel. Optionally, the sealing is pierced through for performing the fluid extraction process and for pulling the absorbing member through the cap.

All dimensions of the components mentioned above are exemplary, and may be adjusted to any larger, smaller, or intermediate dimensions, as long as they are proportioned such as to fit together within the box.

Figure 7:
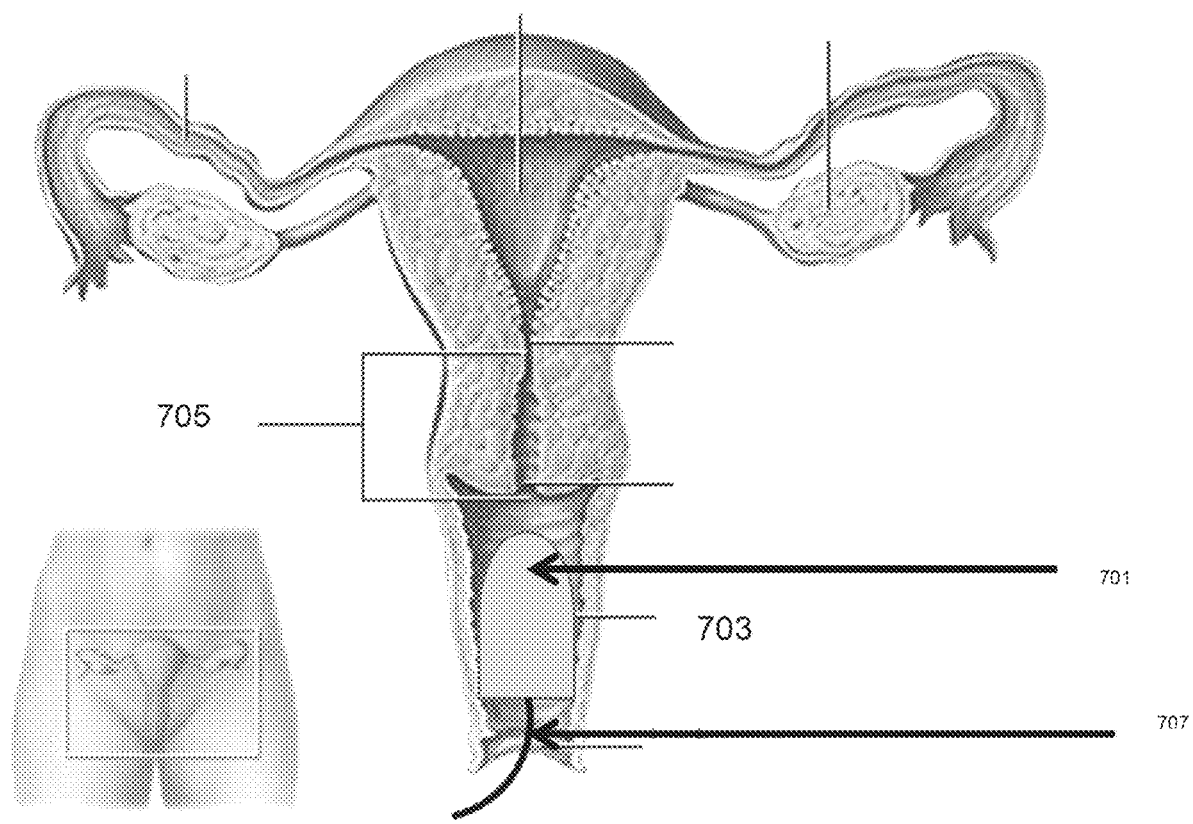
FIG. 7 is an illustration of an absorbing member inserted into a vagina for collecting fluid, according to some embodiments of the invention.

FIG. 7 is an illustration of an absorbing member 701 inserted into a vagina 703 for collecting fluid, according to some embodiments of the invention. A cord 707 is maintained externally to the vaginal opening, for example to facilitate removal of absorbing member 701.

In some embodiments, fluid is collected from the vaginal area. In some embodiments, the fluid comprises cells. Optionally, the cells are cervical tissue 705 cells that were collected by fluid flowing towards absorbing member 701. Optionally, the movement of cells towards the vagina changes a shape and/or size of the cells. A potential advantage of the method may include analyzing cell content (for example by bursting the cells that are contained in the fluid) of deformed cells that would have been hard or impossible to analyze using common cytology techniques.

FIGS. 8A-C are drawings of a sample container comprising an extracting element for extracting fluid from an absorbing member, according to some embodiments of the invention. FIG. 8A shows a side view of a sample container. FIG. 8B shows a cross section view of the sample container along section A-A of the container, as indicated in FIG. 8A, and FIG. 8C shows a top view of an extracting element 103 (for example as observed from the top of the container). In some embodiments, one or more extracting elements 803 are configured within container 801. In some embodiments, the extracting elements are positioned within the container so as to form an aperture small enough to squeeze the absorbing member 805 as it is passed through the container, for example during pulling of the absorbing member out of the container and/or insertion of the absorbing member into the container.

In some embodiments, the extracting elements are attached to the container walls, for example mounted using adhesives or connected by any other attachment means.

In some embodiments, an extracting element extends circumferentially around the container walls, for example being shaped as an "o-ring" 803, as shown in this figure. In some embodiments, an extracting element comprises other shapes, for example being shaped as a rod that is attached to the container wall, which narrows a passage within the container along at least a portion of the container.

In some embodiments, the extracting element comprises slots and/or pores for causing the fluid that collects on a surface of the extracting element to drip and/or flow down, for collecting the fluid. Optionally, the collected fluid adds to the preserving solution within the container.

In some embodiments, the extracting element is made of a relatively hard material, such as plastic. Alternatively, the extracting element is made of a relatively soft material, such as rubber and/or silicon. Optionally, the extracting element is at least partially compressible for enabling the passage of absorbing member 807 through.

Exemplary dimensions of an extracting member, for example shaped as an "o-ring" may include an external diameter 809 sized according to a diameter of the container, for example ranging between 10-35 mm, and an internal diameter 811 sized according to a size of the absorbing member, for example in its expanded condition, ranging between 12-30 mm.

Figure 9:
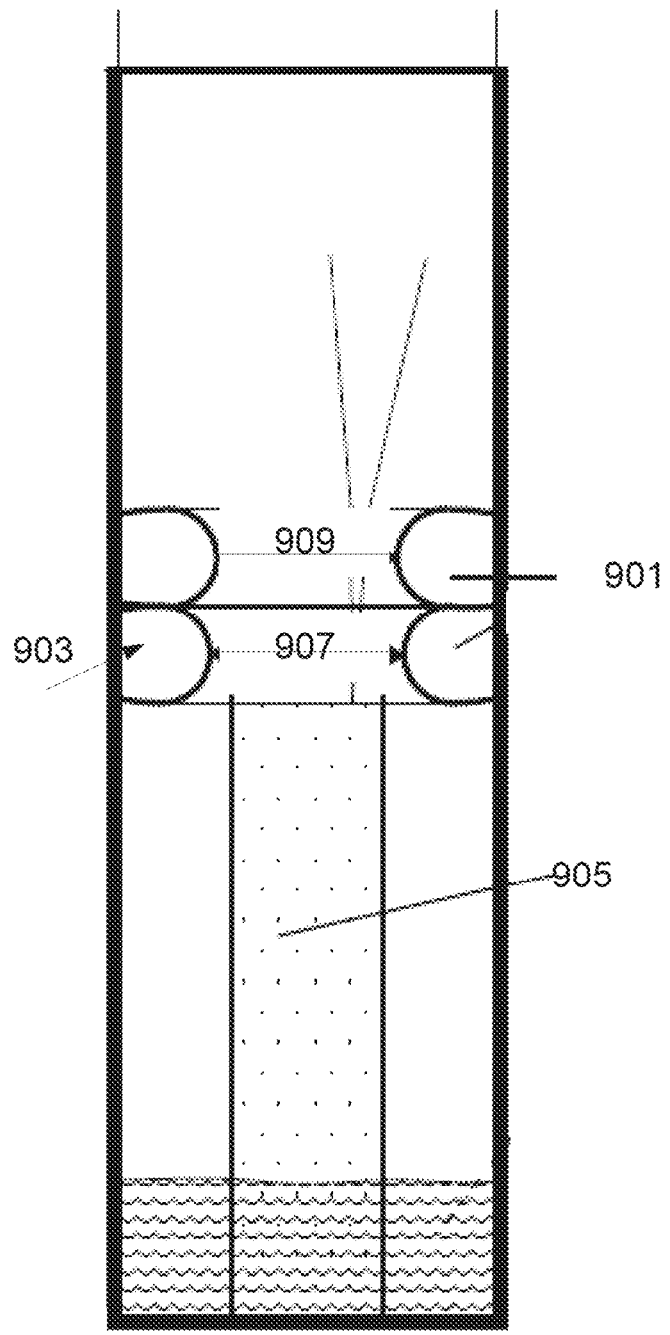
FIG. 9 is a drawing of a container comprising a plurality of extracting elements, according to some embodiments of the invention.
Figure 10A:
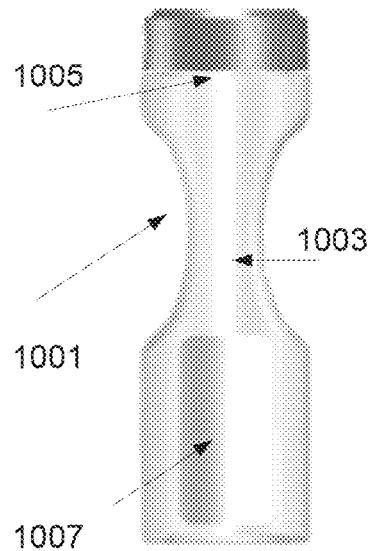
FIGS. 10A-F illustrate various configurations of a container comprising a narrowing, and an exemplary cross section profile of a narrowing, according to some embodiments of the invention.
Figure 10B:
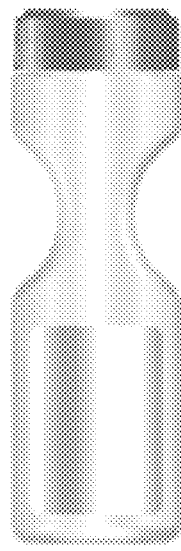
Figure 10C:
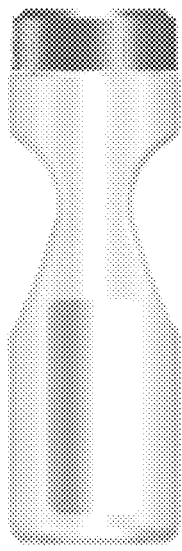
Figure 10D:
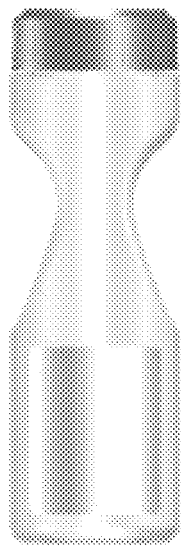
Figure 10E:
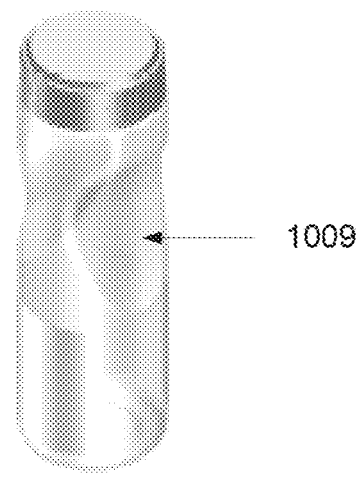
Figure 10F:
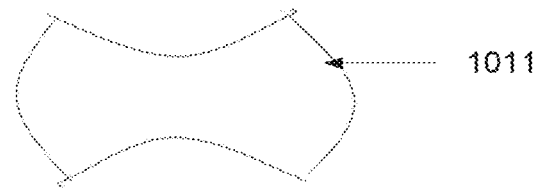

FIG. 9 illustrates a container comprising a plurality of extracting elements, according to some embodiments of the invention. This figure illustrates, for example, a set of two "o-ring" shaped extracting elements 901 and 903, positioned, for example, one on top of the other. In some embodiments, when a plurality of extracting elements are used, each may define a different sized aperture for passing of the absorbing member 905 through. For example, element 903 may define an aperture slightly larger than the aperture of element 901, for example by having an internal diameter 907 larger than diameter 909 of element 901, for example 10%, 20%, 40% larger. Alternatively, diameter 907 can be equal to or smaller than diameter 909. Optionally, the absorbing member is gradually squeezed by both extracting elements, such that upon pulling of the absorbing member towards the opening of the container increased pressure is applied on its walls. In some embodiments, the extracting elements are spaced adjacent to each other, for example as shown in this figure. Alternatively, the extracting elements are spaced apart from each other, for example one extracting element located in proximity to the cap of the container, and another located in proximity to the surface of the preserving solution.

FIGS. 10A-F illustrate various configurations of a container comprising a narrowing, and an exemplary cross section profile of a narrowing, according to some embodiments of the invention. In some embodiments, container 1001 comprises one or more narrowings 1003, for example forming a bottle shaped configuration comprising a neck. Optionally, fluid is extracted from the absorbing member by pulling the absorbing member towards the opening of the container through the narrow portion of the container, which defines an aperture small enough to squeeze the absorbing member as it is pulled through for analysis of the extracted fluid. Optionally, the aperture defined at the narrowing is yet large enough for receiving the absorbing member when it is inserted into the container. Optionally, narrowing 1003 is located in proximity to opening 1005 of the container, for example positioned close enough to the opening so that the surface of preserving solution 1007 does not reach the narrowing. Optionally, fluid extracted by pulling the member through the narrow portion drips and/or slides down the container along the walls of the narrowing. In some embodiments, as shown for example in the isometric view of FIG. 10E, the narrowing is formed by one or more curves 1009 of the container wall, forming an internally facing bulge within the container which defines the narrowing. Optionally, opposite facing curves form the narrowing. Optionally, the narrowing is defined such that its cross section profile does not comprise an even distribution of bulges. Optionally, a non even distribution causes the pressure applied onto the absorbing member by the container walls to be higher along some portions of the absorbing member, and lower along other portions. Optionally, a cross section profile of the narrowing comprises a circular profile, a quadrilateral profile (e.g. squared, rectangular, trapezoidal or any other configuration), or an arbitrary profile. An exemplary cross section profile 1011, shown in FIG. 10F, matches an exemplary narrowing shown in FIG. 10E.

In some embodiments, a length and/or width of the passage defined at narrowing 1003 are determined according to the dimensions of the absorbing member.

In some embodiments, container 1001 is at least partially formed of an elastically deformable material, such as deformable plastics or rubber, for being capable of deforming to produce the narrowing. For example, a user, by applying a squeezing force externally to the container in a radial direction, may push the container walls such that a narrowing is formed. Optionally, during fluid extraction, the user may squeeze and release the container one or more times for applying pressure onto the absorbing member. Optionally, the amount of applied pressure varies, for example a user may apply relatively low pressure during an initial squeezing of the absorbing member, and increasing pressure as the member is advanced towards the container opening. A potential advantage of a squeezable container may include facilitating insertion of the absorbing member by a patient, for example by squeezing the container one or more times or until the absorbing member is fully received within the container.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method for extracting fluid from an absorbing member, comprising:
   providing an absorbing member shaped and sized as a vaginal tampon, said absorbing member absorbed with fluid previously collected from within the vagina, said absorbing member comprising an attached bendable cord; said absorbing member placed in a sample container;
   passing said absorbing member through a narrowing defined by an elastically deformable portion of said sample container, said passing comprising pulling said bendable cord to remove said absorbing member from said sample container and thereby squeeze said absorbing member as said absorbing member passes through said narrowing;
   applying external radial pressure onto said elastically deformable portion to further squeeze said absorbing member to extract fluid; and
   collecting, within said sample container, extracted fluid which accumulates on at least one wall of said sample container as a result of said absorbing member being squeezed.

2. The method according to claim 1, wherein said fluid comprises body fluid and cells and wherein said method further comprises applying a nucleic acid assay to said extracted body fluid and cells to detect pathogenic genomic material.

3. The method according to claim 2, wherein said pathogenic genomic material comprises at least one of viral genome and bacterial genome.

4. The method according to claim 3, wherein said viral genome includes at least one of human papillomavirus mRNA and human papillomavirus DNA.

5. The method according to claim 2, wherein said body fluid and cells were collected from a vagina.

6. The method according to claim 2, wherein passing said absorbing member through said narrowing comprises bursting open cells and releasing contents of said cells.

7. The method according to claim 1, wherein radial pressure is applied onto said absorbing member during said passing through said narrowing.

8. The method according to claim 1, wherein passing said absorbing member through said narrowing reduces a size of at least a portion of a swollen absorbing member.

9. The method according to claim 1, wherein fluid extracted from said absorbing member is collected within said sample container.

10. The method according to claim 9, wherein said extracted fluid blends in a preserving solution within said sample container.

11. The method according to claim 1, comprising, placing said absorbing member in a preserving solution inside said sample container.

12. The method according to claim 1, wherein said external radial pressure is applied manually.

13. The method according to claim 1, wherein said applying of external radial pressure pushes said elastically deformable portion to thereby apply radial pressure onto said absorbing member.

14. The method according to claim 2, wherein an amount of said body fluid and cells collected by said extracting is sufficient to improve a sensitivity of said nucleic acid assay by at least 10% as compared to a sensitivity of a nucleic acid assay performed on cells only.

* * * * *